US00PP11857P2

(12) United States Plant Patent
Fleming et al.

(10) Patent No.: US PP11,857 P2
(45) Date of Patent: May 1, 2001

(54) HIBISCUS PLANT NAMED 'CROWN JEWELS'

(75) Inventors: David W. Fleming; Gretchen A. Zwetzig, both of Lincoln, NE (US)

(73) Assignee: Fleming's Flower Fields, Inc., Lincoln, NE (US)

( * ) Notice: Subject to any disclaimer, the term of this patent is extended or adjusted under 35 U.S.C. 154(b) by 0 days.

(21) Appl. No.: 09/289,836

(22) Filed: Apr. 12, 1999

(51) Int. Cl.[7] ..... A01H 5/00

(52) U.S. Cl. ..... Plt./257
(58) Field of Search ..... Plt./257

*Primary Examiner*—Bruce R. Campbell
*Assistant Examiner*—Wendy A Baker

(57) ABSTRACT

A new and distinct cultivar of winter hardy hibiscus plant named, 'Crown Jewels' is the result of a unique hybridization. This new and distinct cultivar is characterized primarily as to its low-growing nature, its extreme cold hardines to Zone 4, its dark purple "maple-cut leaf", its ruffled white flowers with red partially-streaking centers, and its vigorous and uniform growth habit, and its floriforous nature from midsummer until frost.

3 Drawing Sheets

BACKGROUND OF THE NEW PLANT

The new plant of this invention is the result of a unique hybridization, with the breeding achievement being evidenced in the outstanding combination of characteristics exhibited by this new and distinct hibiscus plant, which include:

(a) Refined, uniquely colored and compact 3-lobed leaves with a "maple-cut" which have relatively smooth margins and an evenly distributed dark purple-violet coloring that compliments the landscape;
(b) Medium sized flowers that are outstanding for their white, thick-textured petals with red centers that streak through veination to halfway to the petal edges which have a pink blush of color;
(c) The plant being floriferous with flowers that stay open at least one full day;
(d) The plant being low-growing, but vigorous, with compact and uniform breaking action which gives it unique landscape utility;
(e) The plant being so hardy that it can consistently withstand winter temperatures of at least −30 degrees Fahrenheit.

SUMMARY OF THE INVENTION

'Crown Jewels' was the result of a 40-year breeding program. It's ancestry includes *Hibiscus moscheutos* and *Hibiscus coccineus*. More specifically, the seed parent of the instant plant is an un-named cultivar resulting from the cross of 'Dahliatown Orchid' (unpatented) (seed parent) and an unknown pollen parent. The pollen parent of the instant plant is an unnamed *H. coccineus*.

This new plant first bloomed in the summer of 1989 and was selected by David Fleming and Gretchen Zwetzig on the property in Lincoln, Nebr., owned by David Fleming. Asexual propagation of the plant by cuttings and root division in Lincoln, Nebr., has shown that the unique and distinguishing features of the plant are faithfully transmitted from generation to generation and appear to be firmly fixed.

Since its origin, the plant has loomed from midsummer until frost, while exhibiting the above mentoned distinctive characteristics. This hardy hibiscus plant contributes to the market with its sheer beauty, its low-growing and very compact growth habit, its great resistance to disease and insects, its stability through extremes in rain and drought, and its extreme hardiness.

BRIEF DESCRIPTION OF THE DRAWINGS

The flower, bud, foliage, and growth habit of the plant are shown in the attached illustrations.

More specifically, the first drawing shows the bloom and buds in varying stages of maturity and the foliage and the growth habit of the cultivar. The second drawing depicts the bud and foliage in greater detail.

The third drawing is a close-up view of the flower and the foliage. The colors illustrated are as true as is reasonably possible to attain in photographic illustrations of this type. The colors illustrated may be slightly off due to light reflectance.

DESCRIPTION OF THE NEW PLANT

What follows is a detailed description of the new cultivar. The specific color designations set forth by PLATE number designations are in accordance with the *Dictionary of Color* (Maerz and Paul), while general color recitations are consistent with ordinary American color terminology.

'Crown Jewels' has not been observed under all possible environmental conditions. It is to be understood that the phenotype may vary significantly with variations in environment such as temperature, light intensity, and day length, without, however any difference in genotype of the plant. The following botanical characteristics and observations are taken from a 7 year-old plant when grown under normal outdoor conditions in Lincoln, Nebr.

THE PLANT

Type of plant: Hardy, Herbaceous perennial.
Classification: Hybrid Hibiscus plant.
Propagation: Relatively easy to propagate; fast rooting; holds its distinguishing characteristics through successive propagations by cuttings and division.
Size: No more than 24 inches tall; about 24 inches wide.

Form: Symmetrical annual growth from perennial roots. Plant reaches a mature size (height and spread) in 2 years.

Habit: Upright and uniformly branched.

Growth: Vigorous; short and compact.

Hardiness: Hardy to at least −30 degrees Fahrenheit. Heat tolerant to about 110 degrees Fahrenheit.

General health: Plant is highly resistant to fungal diseases; highly resistant to pests such as Japanese beetle, white flies, aphids and spider mites; sturdy through excessive drought or water.

Foliage:

1. *Arrangement.*—Alternate.
2. *Shape.*—Juvenile — Palmate, refined, 3-lobed leaf. Mature — Very refined, palmate to hastate, 3-lobed leaf with smooth sinuses and acute spices; rounded to cordate base; compact.
3. *Size.*—Mature leaf — (petiole base to apex) length is about 4½ inches (12.5 cm), width is about 3½ inches (8.5 cm).
4. *Color.*—Young leaves (upper side — 6-J, page 119 and 6-H, page 135, PLATE 48; background green 4-J, page 135, PLATE 24. Mature leaves (upper side) — Old Lavender, 7-A, page 135, PLATE 56; background green 4-J, page 71, PLATE 24. Veins — 1-L, page 119, PLATE 48. Underside of mature leaves — 5-E, page 67, PLATE 22.
5. *Surface texture.*—Glabrous with some luster.
6. *Petiole length.*—About 3 inches (7.5 cm).
7. *Petiole color.*—1-L, page 119, PLATE 48.

Stems: The stems are stout at the base, becoming more slender toward the apices; coloration is similar to that of the petiole, towards the top of the stem, and is medium green with some staining due to anthocyanin at the base.

THE FLOWER

Blooming period: Profuse from midsummer until frost.

Flower diameter: Medium; about 5½ inches (13 cm) to 6½ inches.

Borne. Singly in leaf axils, from midpoint of stems upward.

Bloom duration: Individual bloom lasts one full day at least; sometimes two. Typically, the plant displays 5 to 25 blooms at once in a landscape setting, depending on light conditions.

Form: Flat; 5 petals, very overlapping.

Bud:

1. *Length.*—About 1¾ inches (4.5 cm). Diameter 1 to 1½ inches.
2. *Color.*—1-I, page 57, PLATE 17; veins — 6-E, page 37, margin — 5-J, page 37, Plate 5.
3. *Duration.*—One to two weeks.

Corolla:

1. *Petal character and dimensions.*—Semi-ruffled and very overlapping. Length is about 2¾ inches (7 cm). Width is about 4 inches (10 cm).
2. *Coloration.*—White with red center or eye (about 2 inches in diameter) and red streaking extending outward from eye to midway between the eye and the edge of the petals; the petal edges have a "blush" of pink, (a). White petals — 1-A, page 27, PLATE 2 and 2-A, page 27, PLATE 2. (b). Petal margins (overall effect): 5-J, page 33, PLATE 5. (c). Veination in petals: 6-E, page 37, PLATE 7. (d). Eye zone — 6-K, page 33, PLATE 5 (inner), and 6-L, page 33, PLATE 5.
3. *Texture.*—Smooth.
4. *Substance.*—Thick.
5. *Shape.*—Ruffled and very overlapping: campanulate.

Reproductive organs:

1. *Staminal column.*—Stamen along basal two-thirds. Stamen length — About 11/2 inches (4 cm). Stamen color — 1-A, page 25, PLATE 1. Pollen color — 2-E, page 41, PLATE 9.
2. *Style.*—Terminates upper one-third of Staminal column. Stigmatic lobe color — 1-J, page 43, PLATE 10.

Calyx: Connate at the base; about 1 inch (3 cm) in length. Stipules: None.

Epicalyx: Whorl of Bracts.

1. *Shape.*—8–12 slender, sword-shaped bractlets.
2. *Length.*—About 1 inch (2.5 cm).
3. *Color.*—5-J, page 67, PLATE 22; tips 4-E, page 39, PLATE 8.

Peduncles:

1. *Length.*—About 2 inches (5 cm).
2. *Strength.*—Stiff and sturdy.

Fruit/Seed: Seed set is minimal. Round seeds, about 1 cm in diameter, appear in rows inside of a rounded pod.

GENERAL OBSERVATIONS

This plant, as a hybridized hardy Hibiscus, is valuable to the landscape market for decreased heighth, thicker textured and uniquely colored flowers, refined purple-colored "maple-cut" foliage, all-around vigor, full, compact, shrub-like branching habit and adaptation to extreme environments, including the ability to survive winter temperatures of at least −30 degrees Fahrenheit.

We claim:

1. A new and distinct cultivar of hibiscus plant, as herein shown and described, characterized by its short stature, its bold purple "maple-cut" foliage, its ruffled white flowers with red center and red streaking halfway to the petal edges, its vigor, and its hardiness.

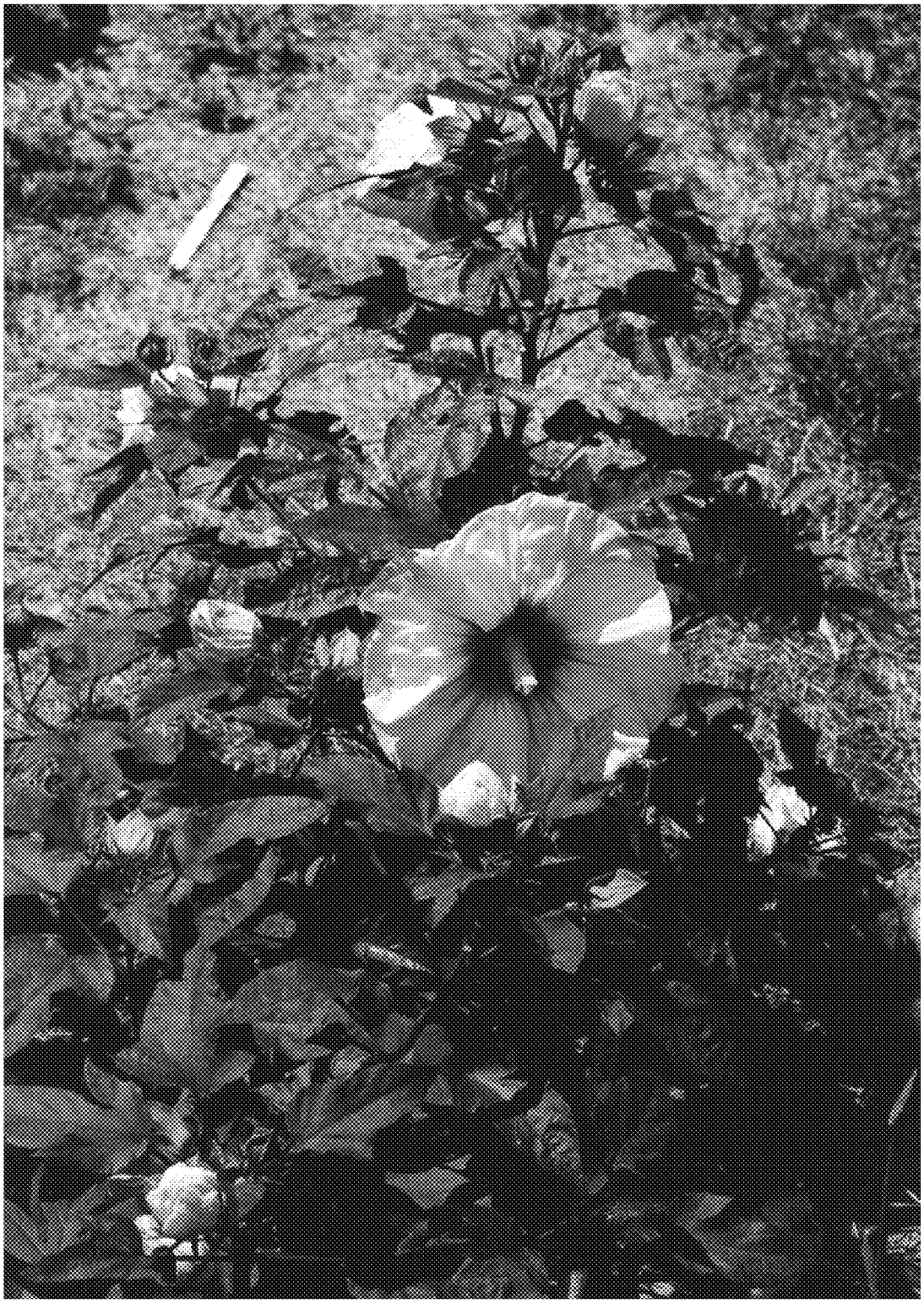

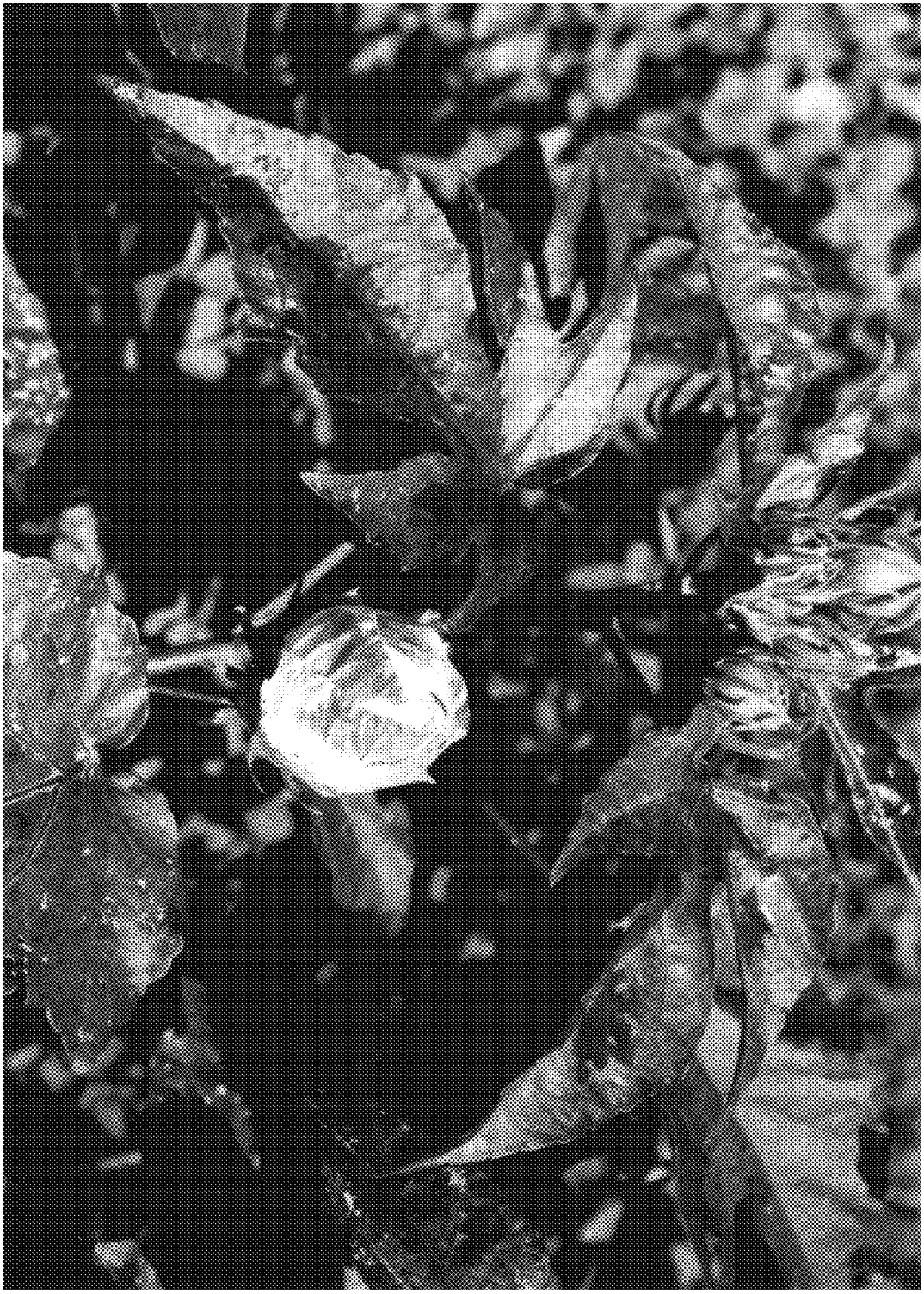

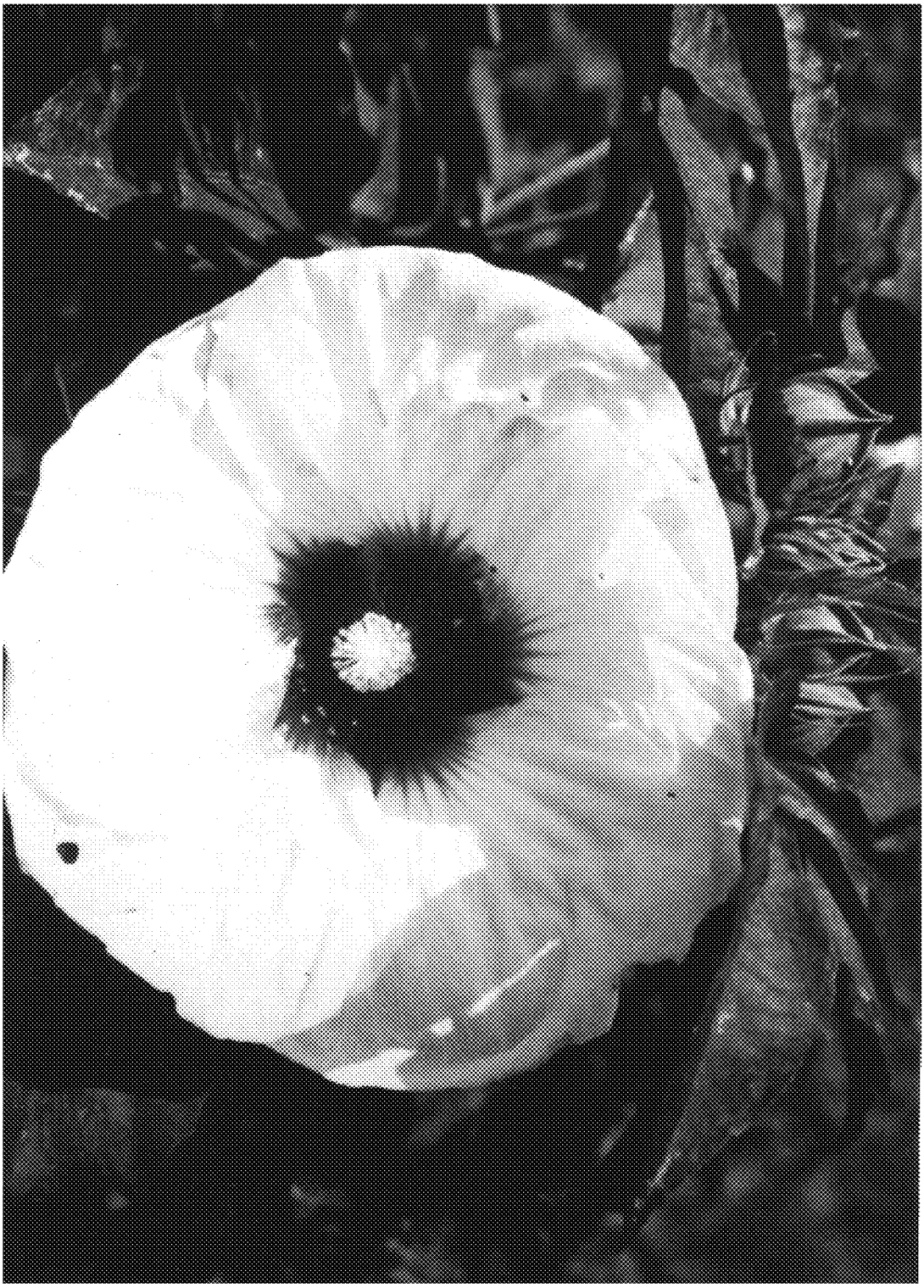

* * * * *